United States Patent [19]
Curtis et al.

[11] Patent Number: 5,962,018
[45] Date of Patent: Oct. 5, 1999

[54] METHOD OF TREATING THE SKIN WITH ORGANIC ACIDS IN ANHYDROUS MICROSPHERE DELIVERY SYSTEMS

[75] Inventors: Ernest S. Curtis, Milford, Pa.; Robert Kalafsky, Ogdensburg; Elinor R. Kaplan, Paterson, both of N.J.

[73] Assignee: Avon Products, Inc., New York, N.Y.

[21] Appl. No.: 09/069,089

[22] Filed: Apr. 28, 1998

[51] Int. Cl.$^6$ .......................... A61K 9/127; A61K 31/19
[52] U.S. Cl. .......................... 424/450; 514/557; 514/574
[58] Field of Search .............................. 424/450; 514/557, 514/574

[56] References Cited

U.S. PATENT DOCUMENTS

| | | |
|---|---|---|
| 3,920,835 | 11/1975 | Van Sott et al. . |
| 4,045,559 | 8/1977 | Roman . |
| 4,053,630 | 10/1977 | Yu et al. . |
| 4,194,007 | 3/1980 | Van Scott et al. . |
| 4,363,815 | 12/1982 | Yu et al. . |
| 4,849,458 | 7/1989 | Reed et al. . |
| 4,873,308 | 10/1989 | Coury et al. . |
| 5,000,955 | 3/1991 | Gould et al. . |
| 5,118,779 | 6/1992 | Szycher . |
| 5,254,662 | 10/1993 | Szycher et al. . |
| 5,292,512 | 3/1994 | Schaefer et al. . |
| 5,334,691 | 8/1994 | Gould et al. . |
| 5,489,431 | 2/1996 | Ascione et al. . |
| 5,496,565 | 3/1996 | Heinze et al. . |
| 5,605,933 | 2/1997 | Duffy et al. . |
| 5,667,765 | 9/1997 | Hansenne et al. . |

FOREIGN PATENT DOCUMENTS

WO96/10992  4/1996  WIPO .

*Primary Examiner*—William R. A. Jarvis
*Attorney, Agent, or Firm*—Ohlandt, Greeley, Ruggiero & Perle, LLP

[57] ABSTRACT

There is provided a method of treating skin with a therapeutic, water-soluble organic acid. There is also provided an anhydrous composition containing the water-soluble organic acid is encapsulated into hydrophobic microspheres through which the organic acid can elute in the presence of water is applied to the skin. The composition is wet with water immediately prior to, or after the composition is applied to the skin.

20 Claims, No Drawings

METHOD OF TREATING THE SKIN WITH ORGANIC ACIDS IN ANHYDROUS MICROSPHERE DELIVERY SYSTEMS

BACKGROUND OF THE INVENTION

1. Field of the Invention

The present invention relates to a method of treating the skin with therapeutic organic acids. More specifically, the present invention relates to a method of treating the skin with water soluble organic acids in which a composition containing the water soluble organic acids is encapsulated in microspheres through which the organic acids elute in the presence of water.

2. Description of the Prior Art

Many organic acids, such as alpha-hydroxy acids, beta-hydroxy acids, keto-acids, di-alpha-hydroxy acids and poly-hydroxy carboxylic acids are known to be useful in the treatment of skin conditions. These organic acids, referred to collectively as "therapeutic organic acids", can be used to topically treat skin conditions attributed to, accompanied by or exacerbated by abnormal desquamation. Such conditions include, for example, dry skin, ichthyosis, palmar and plantar hyperkeratoses, dandruff, lichen simplex chronicus, Dariers disease, keratoses, lentigines, age spots, melasmas, blemished skin, acne, psoriasis, eczema, pruritis, inflammatory dermatoses, striae distensae (i.e., stretch marks), warts and calluses.

Therapeutic organic acids are useful active agents in topical preparations for treating signs of dermatological aging, i.e. photoaging and intrinsic aging, including skin wrinkles such as fine wrinkles around the mouth area, irregular pigmentation, sallowness and loss of skin resilience and elasticity.

Therapeutic organic acids and topical compositions containing therapeutic organic acids are also useful for treating disorders associated with nails, cuticles and hair such as ingrown hair, folliculitis, and Pseudofolliculitis barbae. These therapeutic organic acids also soften hair and aid in the elimination of ingrown hairs, thus making therapeutic organic acids useful as components in shaving compositions.

Although useful in the treatment of a number of skin conditions, effective levels of therapeutic organic acids cannot generally be provided in stable, anhydrous compositions. Thus, a method of treating the skin with effective levels of therapeutic organic acids, in which the organic acid can be topically delivered to the skin in a stable anhydrous composition, has remained unavailable.

SUMMARY OF THE INVENTION

An object of the present invention is to provide a method of topically treating the skin with effective levels of a therapeutic, organic acid-containing composition that is available as a stable, easily produced anhydrous product.

A further object of the present invention is to provide such a method in which the therapeutic organic acids can be applied in a time-released manner to provide a long lasting treatment.

These and other objects will become apparent to those skilled in the art after having the benefit of the present invention.

To accomplish the foregoing objects and advantages, the present invention, in brief summary, is a method of treating skin with therapeutic organic acids in which a composition including the water-soluble therapeutic organic acid encapsulated in microspheres through which the organic acid can elute in the presence of water, is applied to the skin. Preferably, the composition is anhydrous. The composition is wet with water immediately prior to, or after applying the composition to the skin.

DETAILED DESCRIPTION OF THE PREFERRED EMBODIMENT

The present invention provides for one or more therapeutic, water soluble organic acids encapsulated within one or more microspheres. The microspheres can be easily combined with anhydrous base materials to form stable compositions. The compositions are contacted with water immediately before or after being applied to the skin at which time the organic acids elute from the microspheres in a non-degraded form and are absorbed by the skin.

The therapeutic organic acids can include one or more carboxylic acids including alpha-hydroxy acids, beta-hydroxy acids, di-alpha-hydroxy acids and keto-acids, all of which as a group are commonly referred to as AHAs (alpha-hydroxy acids). Such AHAs are described in detail in, for example, U.S. Pat. Nos. 3,920,835; 4,045,559; 4,053,630 and 4,363,815, the disclosures of which are all incorporated herein by reference. Suitable therapeutic organic acids may also include derivatives of retinoic acid, such as α-hydroxyretinoic acid and α-ketoretinoic acid, as described in U.S. Pat. No. 4,194,007, the disclosure of which is also incorporated herein by reference. Suitable therapeutic organic acids may also be poly-hydroxy carboxylic acids and the oxa acids and oxa diacides disclosed in U.S. Pat. No. 5,847,003, which issued on Dec. 8, 1998, and U.S. Pat. No. 5,834,513, which issued Nov. 10, 1998, respectively, the subject matter of which is also incorporated herein by reference. The therapeutic organic acids can be incorporated into the microspheres as free acids or as corresponding salts derived by neutralization with organic or inorganic bases, such as triethanolamine arginine, lysine, potassium hydroxide, sodium hydroxide, lithium hydroxide or ammonium hydroxide.

Pursuant to the present invention, the water-soluble organic acid is encapsulated within a polymeric microsphere. Polymeric microspheres are used in a number of the currently available transdermal patches to release a medication into the skin in a time released manner. A preferred microsphere is formed of a non-polar copolymer of carbamate and acrylate, and is available from Brook Industries, South Plainfield, N.J., and sold under the trade name of ChronoSphere®. Chronosphere® brand polymeric microspheres are formed by mixing a urethane oligomer, a photoinitiator, a liquid acrylate and the material to be entrapped, i.e. the organic acid; casting the mixture into a film; and, exposing the film to ultraviolet (UV) radiation. Once cured, the polymer forms a homogeneous polymer that can be made in a microparticle size, i.e. an average size about 20 to about 40 microns.

Each microparticle or microsphere can contain from about 20 wt. % to 30 wt. % of the entrapped materials. Under certain circumstances active loading levels up to 50 wt. % have been achieved. The microspheres are insoluble in both water and oil. Also, the loaded microspheres are pressure insensitive and cannot be crushed under normal processing, packaging or subsequent handling conditions.

A further advantage of microsphere-encapsulated organic acids is that the therapeutic organic acids elute slowly from the microspheres in the presence of water. The time over which the organic acids diffuse from the microspheres can be controlled based on, for example, the level at which the organic acid is loaded into the microspheres, and the physical characteristics of the microspheres. The slow elution of the therapeutic organic acids provides a time release effect that can be customized depending on the organic acid and the skin condition that is to be treated.

The microsphere-encapsulated therapeutic organic acid can be applied to the skin in the form of a dry powder, an anhydrous solid, an anhydrous cream, an anhydrous lotion or anhydrous gel. When in the form of a lotion, cream, solid or gel, the microsphere-encapsulated organic acid is formulated into an anhydrous base material or vehicle. Anhydrous base materials or vehicles include all physiologically acceptable anhydrous bases or vehicles, i.e. non-toxic anhydrous materials that can be placed in direct contact with human tissue. Specific examples of suitable anhydrous base materials or vehicles include hydrocarbon oils, esters, silicon oils, polyols, alcohols, fluorinated hydrocarbons, waxes (for forming solid sticks) and in the case of dry powders, talc and mica.

The efficacy of the microsphere-encapsulated therapeutic organic acid in the treatment of skin conditions has been found to be affected by the pH of the composition and the pKa of the acid. It is desirable to maintain the pH of the composition in the acid range of pH <7.0, preferably pH <5.0, most preferably in the pH range from about 3.5 to about 4.0. It is also preferable to maintain pH of the composition at a level that is substantially the same as the pKa of the therapeutic organic acid encapsulated within the microspheres. The pH of the topical composition containing the microsphere encapsulated therapeutic organic acid can be adjusted by adding water soluble salts of strong bases (e.g., KOH, NaOH, $NH_4OH$) and weak acids (e.g., phosphoric acid, acetic acid, lactic acid, carbonic acid). Examples of suitable salts include potassium biphosphate, sodium phosphate, sodium acetate, sodium lactate and the like. Other conventional methods of adjusting the pH of topical compositions are well known in the art and can also be used to adjust the pH of the topical compositions applied to the skin in the method of the present invention.

The amount of microsphere-encapsulated therapeutic organic acid in the topical composition will depend on a number of variables including the condition being treated, the severity of the condition and the age and physical condition of the person being treated. Other factors may include the specific organic acid or acids employed, the base material or vehicle used to deliver the organic acid, the duration of treatment and the nature of any concurrent treatments. Generally, the therapeutic organic acid or acids will comprise from about 0.1 wt. % to about 70 wt. %, preferably from about 0.10 wt. % to 50 wt. %, most preferably from about 0.10 wt. % to about 30 wt. % of the total weight of the microsphere encapsulated organic acid (based on the total weight of therapeutic organic acid and the polymer of the microspheres). When the microsphere-encapsulated organic acid is formulated into an anhydrous base material or vehicle, the microsphere-encapsulated organic acid (including the weight of the therapeutic organic acid and the polymer of the microspheres) will comprise from about 0.1 wt. % to about 80 wt. %, preferably from about 1 wt. % to about 30 wt. %, most preferably from about 1 wt. % to about 20 wt. %, based on the total weight of the composition.

The microsphere-encapsulated therapeutic organic acid used in accordance with the method of this invention can be incorporated into any composition intended for topical use in any cosmetic, dermatological or pharmaceutical utility. The microsphere encapsulated therapeutic organic acid can be readily used in compositions containing other cosmetic and pharmaceutical agents, e.g. anti-fungals, vitamins, sunscreens, retinoids, antihistamines, depigmenting agents, anti-inflammatory agents, anesthetics, surfactants, emulsifiers, stabilizers, preservatives, antiseptics, emollients, thickeners, lubricants, humectants, chelating agents, fragrances, colorants and skin penetration enhancers.

The microsphere-encapsulated therapeutic organic acid can be used in combination with one or more emulsifiers. The emulsifiers can be anionic, nonionic, cationic or amphoteric, or a combination thereof. A nonionic emulsifier is preferred. Examples of nonionic emulsifiers are commercially available sorbitans, alkoxylated fatty alcohols, and alkyl polyglycosides. Examples of anionic emulsifiers are alkyl sulfates, monoalkyl and dialkyl phosphates, alkyl sulphonates and acyl isethionates. Examples of cationic emulsifiers are quarternium salts, cetrimonium chloride and laurtrimonium chloride. Examples of amphoteric emulsifiers are cocamidopropyl betaine, coco betaine, myristamidopropyl betaine and oleyl betaine. Other suitable emulsifiers are described in literature such as in McCutcheon's *Detergents and Emulsifiers,* North American Ed., pages 317–324 (1986), which is incorporated herein by reference.

A preservative may be used with the microsphere-encapsulated therapeutic organic acid of the present invention. Such preservatives useful in the practice of the present invention include parabens, sorbates, benzyl alcohol, diazolidinyl urea and isothiazolinones. One or more preservatives can be present in a total amount from about 0.001 wt. % to about 15 wt. % of the total composition (the microsphere encapsulated therapeutic organic acid plus all other ingredients).

One or more emollients can be used with the microsphere-encapsulated therapeutic organic acid of the present invention. Examples of emollients suitable for use include silicone oils, such as cyclomethicone/dimethicone copolyol and cyclotetramethicone, mineral oil, cocoa butter, fatty acids esters, beeswax and lanolin. The one or more emollients are present in a total amount from about 5 wt. % to about 50 wt. % of the total composition. Other suitable emollients are described in literature such as *Sagarin, Cosmetics, Science and Technology,* 2nd Ed., vol. 1, pages 32–43 (1972), which is incorporated herein by reference.

A thickening agent may be used with the microsphere-encapsulated therapeutic organic acid of the present invention. Examples of such suitable thickening agents include hydroxypropyl cellulose, clays, bentonite and heavy metal stearate. The thickening agent comprises from about 0.01 wt. % to about 50 wt. %, preferably from about 0.1 wt. % to about 20 wt. %, of the total composition.

A composition containing a microsphere-encapsulated therapeutic organic acid may also include from about 0.10 wt. % to about 50 wt. %, preferably about 0.1 wt. % to about 20 wt. %, of humectants, such as urea.

A composition containing a microsphere-encapsulated therapeutic organic acid of the present invention may also include: from about 0.1 wt. % to about 30 wt. %, preferably from about 0.1 wt. % to about 20 wt. %, keratolytic agents, such as salicylic acid and benzoyl peroxide; from about 0.01 wt. % to about 10 wt. %, preferably from about 0.01 wt. % to about 5 wt. % skin lightening agents, such as kojic acid, hydroquinone and licorice extract; from about 0.1 wt. % to about 50 wt. %, preferably from about 0.1 wt. % to about 35 wt. %, organic and inorganic sunscreens, such as butylmethoxydibenzoyl-methane, titanium dioxide, zinc oxide, benzylidene camphor, salicylates and cinnamic acid derivatives; and from about 0.1 wt. % to about 10 wt. %, preferably from about 0.1 wt. % to about 5 wt. %, quinoline derivatives, quinine salts, uric and violuric acids, tannic acid and its derivatives, hydroquinone, dioxybenzone, benzoresorcinol, 2,2,4,4-tetrahydroxybenzophenone, etocrylene.

A composition that uses the present invention may also include: from about 0.01 wt. % to about 30 wt. %, preferably from about 0.05 wt. % to about 5 wt. %, retinoids, such as retinol, retinoic acid, retinyl palmitate, retinyl propionate or retinyl acetate as well as synthetic retinoid mimics; from about 0.001 wt. % to about 10 wt. % hormones such as estriol or estradiol; and from about 0.01 wt. % to about 60 wt. %, preferably from about 0.01 wt. % to about 30 wt. %, vitamins (e.g. vitamin K, vitamin E, vitamin E acetate).

A composition that contains the present invention may include: from about 0.01 wt. % to about 30 wt. %, preferably from about 0.05 wt. % to about 5 wt. %, anti-fungals (e.g. clotrimazole, ketoconazole, miconazole, naftifine, tolnaftate); from about 0.1 wt. % to about 30 wt. %, preferably from about 0.5 wt. % to about 10 wt. %, self-tanning agents (e.g. dihydorxyacetone, lawsone); from about 0.001 wt. % to about 10 wt. %, preferably from about 0.001 wt. % to about 4 wt. % cortico-steriods; from about 0.001 wt. % to about 20 wt. %, preferably from about 0.005 wt. % to about 5 wt. %, antibiotics (e.g. erythromycin, tetracyclin, cephalosporins); from about 0.1 wt. % to about 40 wt. %, preferably from about 0.5 wt. % to about 25 wt. % topical analgesics (e.g. lidocane); from about 0.5 wt. % to about 10 wt. %, preferably from about 0.001 wt. % to about 20 wt. %, ceramides; from about 0.01 wt. % to about 50 wt. %, preferably from about 0.05 wt. % to about 5 wt. %, essential fatty acids; and from about 0.01 wt. % to about 25 wt. %, preferably from about 0.1 wt. % to about 20 wt. %, (ω-hydroxy fatty acids.

The present invention can also be used in a composition that has from about 0.001 wt. % to about 20 wt. %, preferably from about 0.05 wt. % to about 5 wt. %, topical anti-inflammatory agents that reduce inflammation caused by UV exposure, such as steroidal anti-inflammatories and non-steroidal anti-inflammatories. Examples of steroidal and non-steroidal anti-inflammatories can be found in texts, such as Rainsford, *Antiinflammatory and AntiRheumatic Drugs,* vols. I–III, CRC Press, Boca Raton, Fla. (1985), which is incorporated herein by reference. Specific examples of other suitable anti-inflammatories include enolic acids, oxicams, fenamic acid derivatives, flufenamic acid derivatives, propionic acid esters, pyrazolidinediones and salicylic acid derivatives, such as aspirin, safaprin, disalacid, benorylate and trisilate.

Compositions containing microsphere-encapsulated therapeutic organic acid of the present invention may also include from about 0.001 wt. % to about 40 wt. %, preferably from about 0.05 wt. % to about 20 wt. % of the total composition, safe anti-inflammatory products of natural origin shown to possess anti-inflammatory activity. Those skilled in the art will recognize among such agents, aloe vera extracts, extracts from genus Rubis (*Rubia Cordifolia*), extracts from genus Commiphom (*commphora Mukul*), willow bark, matricarria flowers, arnica flower, comfrey root, fenugreek seed, and the like.

Compositions that use the microsphere-encapsulated therapeutic organic acids of the present invention may include from about 0.001 wt. % to about 50 wt. %, preferably from about 0.05 wt. % to about 25 wt. % of the total composition, antioxidants with phenolic hydroxy functions, such as butylated hydroxytoluene, gallic acid derivatives (e.g. propyl gallate), bioflavonoids (e.g. quercetin, rutin, daidzein, genistein), ferrulic acid derivatives (e.g. ethyl ferrulate, sodium ferrulate), and 6-hydroxy-2,5,7,-tetramethyl-chroman-2-carboxylic acid. The compositions may also contain effective concentrations of water-soluble antioxidants, such as uric acid, reductic acid and tannic acid. Other possible antioxidants that the composition may contain are those which have one or more thiol (–SH) functional groups in either reduced or non-reduced form such as glutathione, lipoic acid, thioglycolic acid and thiolactic acid. The composition may also include inorganic antioxidants, such as sulfites, bisulfites, metbisulfite or other inorganic salts and acids containing sulfur in oxidation state +4.

A composition that includes the microsphere-encapsulated therapeutic organic acids of the present invention may also include from about 0.05 wt. % to about 99 wt. %, preferably from about 0.05 wt. % to about 30 wt. % of the total composition, insect repellents, such as DEET®, other aliphatic, cyclic or aromatic amides, citronella oil, terpineol, cineole, neem oil, terephthalic acid and its esters. Other suitable insect repellents can be found in Technical Bulletin No. 1549 of the U.S. Department of Agriculture or in the USDA Agricultural Handbooks No. 461, 69 and 340, which are incorporated herein by reference.

The microsphere-encapsulated therapeutic organic acids of the present invention may also be in a composition that includes from about 0.01 wt. % to about 50 wt. %, preferably from about 0.1 wt. % to about 20 wt. % base on the weight of the total composition, skin cooling compounds, such as menthol, methyl glycerol, asymmetrical carbonates, thiocarbonates and urethanes, N-substituted carboxamides, ureas or phosphine oxides as described in *J. Cosmet. Chem.,* vol. 29, page 185 (1978) and incorporated herein by reference, methyl lactate and menthone glycerin acetal.

EXAMPLE 1

An anhydrous powder (with cosmetic color) made in accordance with the present invention includes the following, expressed as percents of total weight of the entire powder composition:

| Ingredient | Function | wt. % |
|---|---|---|
| Sericite 100 (lecithin treated) | Filler | 14.57 |
| Sericite-Silicone | Treated Powder* | 4.0 |
| Talc (lecithin treated) | Treated Powder | 20.0 |
| ChronoSpere Triple AHA** | Encapsulated Active | 10.0 |
| Bismuth Oxychloride-UVR | Pearl | 3.0 |
| Zinc Stearate | Powder Binder | 4.0 |
| Nylon Powder | Treated Powder | 6.0 |
| Methylparaben | Preservative | 0.3 |
| Imidazolidinyl Urea | Preservative | 0.2 |
| Titanium Dioxide | Color | 6.0 |
| Dimethyl/Trimethyl Polysiloxane | Liquid Binder | 5.7 |
| PVP/Eicosene Copolymer | Liquid Binder | 0.3 |
| Dimethicone/Dimethiconol (87/13%) | Liquid Binder | 2.0 |
| Ethylhexyl-Methoxycinnamate | Liquid Binder | 1.0 |
| Sorbitan Sesquioleate | Liquid Binder | 0.3 |
| Squalane | Liquid Binder | 2.5 |
| Mica Hydrophobic Silicone | Treated Powder | 20.0 |
| Liposome Vitamin A/C/E/; Beta-Carotene | Vitamin | 0.02 |
| Vitamin A Palmitate | Vitamin | 0.05 |
| Tocopheryl Acetate | Vitamin | 0.05 |
| Total | | 100.00% |

*to provide an improved feel
**Polymer encapsulated AHAs, 24% by weight AHA including 10% lactic acid, 7% tartaric acid and 7% maleic acid (sold by Brooks Industries, South Plainfield, NJ)

EXAMPLE 2

An anhydrous cream made in accordance with the present invention includes the following, expressed as percents of total weight of the cream composition:

| Ingredient | Function | wt. % |
|---|---|---|
| $C_{12}$–$C_{15}$ Alcohols Benzoate | Solvent | q.s. |
| Vegetable Oil Triglyceride | Emollient | 8.25 |
| Sorbitan Sesquioleate | Emulsifier | 0.50 |
| Polyglycerol Diisostearate | Emulsifier | 0.20 |
| Carnuba wax | Wax*** | 6.25 |
| Hydrogenated Coco-Glycerides | Wax*** | 4.25 |
| Ozokerite 170-D | Wax*** | 2.00 |
| Colors | Colors | 15.00 |
| Aluminum Starch Octenylsuccinate | Powder | 11.25 |
| Sericite S-125 | Powder | 11.25 |
| Propylparaben | Preservative | 0.40 |
| Ethylparaben | Preservative | 0.20 |
| Butylparaben | Preservative | 0.07 |
| Chronosphere Triple AHA | Encapsulated Active | 10.00 |
| Total | | 100.00% |

***to provide the composition with structure

EXAMPLE 3

An anhydrous solid (stick) made in accordance with the present invention includes the following, expressed as percents of total weight of the entire solid composition:

| Ingredient | Function | wt. % |
|---|---|---|
| Propylene Glycol Dicaprylate/Dicaprate | Solvent | 38.00 |
| Beeswax | Wax | 9.00 |
| Ozokerite 170-D | Wax | 9.00 |
| Ethylhexyl Palmitate | Emollient | 5.00 |
| Isopropyl Lanolate (Solid) | Emollient | 5.00 |
| Candelilla Wax | Wax | 3.50 |
| Lanolin Wax (Deodorized) | Emollient | 0.50 |
| Butylated Hydroxytoluene | Antioxidant | 0.02 |
| Castor oil (Preserved) | Color Dispersant | q.s. |
| Colors and Pearls | Colors/Pearls | 15.00 |
| Jojoba Oil (Microencapsulated) | Emollient | 0.50 |
| Tocopheryl Acetate | Vitamin | 0.05 |
| Ethylhexyl-Methoxycinnamate | Sunscreen | 1.00 |
| Titanium Dioxide (3 microns) | Sunscreen | 1.00 |
| Total | | 100.00% |

The present invention has been described with particular reference to the preferred forms thereof. It will be obvious that various changes and modifications may be made therein without departing from the spirit and scope of the present invention as defined by the following claims.

What is claimed:

1. A therapeutic composition comprising:
   an anhydrous vehicle selected from the group consisting of powder, lotion, solid, cream and gel;
   at least one microsphere; and
   from about 20 wt %.% to about 30 wt. % of a water-soluble organic acid entrapped within said at least one microsphere
   wherein said at least one microsphere is formed of a non-polar copolymer of a carbamate and an acrylate, and wherein the addition of water to the composition facilitates the elution of said water-soluble organic acid from within said at least one microsphere to without said at least one microsphere.

2. The composition of claim 1, wherein said water-soluble organic acid is selected from the group consisting of alpha-hydroxy acids, beta-hydroxy acids, keto-acids, polyhydroxy carboxylic acids, oxa acids, oxa-diacids and mixtures thereof.

3. A method of treating a skin or hair condition with a therapeutic, water-soluble organic acid, said method comprising:
   applying to the skin or hair an anhydrous composition that includes a water-soluble organic acid encapsulated in one or more microspheres through which said organic acid will elute in the presence of water; and
   wetting said composition with water immediately prior to, or after applying said composition to the skin or hair,
   wherein said skin or hair condition is selected from the group consisting of dry skin, ichthyosis, palmar and plantar hyperkeratoses, dandruff, lichen simplex chronicus, Dariers disease, keratoses, lentigines, age spots, melasmas, blemished skin, acne, psoriasis, eczema, pruritis, inflammatory dermatoses, striae distensae, warts, calluses, ingrown hair, folliculitis, Pseudofolliculitis barbae, photoaging, fine wrinkles, irregular pigmentation, sallowness, loss of skin resilience and loss of elasticity, and
   wherein said microsphere is formed of a non-polar copolymer of a carbamate and an acrylate.

4. The method of claim 3, wherein said composition further comprises an anhydrous base material.

5. The method of claim 3, wherein said water-soluble organic acid is selected from the group consisting of alpha-hydroxy acids, beta-hydroxy acids, keto-acids, polyhydroxy carboxylic acids, oxa acids, oxa di-acids and mixtures thereof in the form of free acids or salts thereof.

6. The method of claim 3, wherein said microspheres are formed of non-polar copolymer of a carbamate and an acrylate.

7. The method of claim 3, wherein said encapsulated water-soluble organic acid is from about 0.1 wt. % to about 70 wt. % of said composition.

8. The method of claim 7, wherein said encapsulated water-soluble organic acid is from about 0.1 wt. % to about 50 wt. % of said composition.

9. The method of claim 3, wherein said composition is in a form selected from the group consisting of dry powders, anhydrous solids, anhydrous lotions, anhydrous creams and anhydrous gels.

10. The method of claim 3, wherein said composition has a pH <7.

11. The method of claim 10, wherein said composition has a pH <5.

12. The method of claim 11, wherein said composition has a pH in a range from about 3.5 to about 4.0.

13. The method of claim 3, wherein said composition further comprises at least one additional agent selected from the group consisting of antifungals, vitamins, sunscreens, keratolytic agents, retinoids, antiallergenic agents, depigmenting agents, antiinflammatory agents, anaesthetics, surfactants, moisterizers, exfolients, emulsifiers, antioxidants, insect repellents sunscreen agents, stabilizers, preservatives, antiseptics, emollients, thickeners, lubricants, humectants, chelating agents, fragrances, colorants and skin penetration enhancers.

14. The composition of claim 1, wherein the composition is for topical application.

15. The composition of claim 1, wherein said water-soluble organic acid is selected from the group consisting of alpha-hydroxy acids, beta-hydroxy acids, keto-acids, di-alpha-hydroxy acids and poly-hydroxy carboxylic acids, derivatives of retinoic acid, poly-hydroxy carboxylic acids, oxa acids, oxa diacids, and mixtures thereof.

16. The method of claim 3, wherein said water-soluble organic acid is selected from the group consisting of alpha-hydroxy acids, beta-hydroxy acids, keto-acids, di-alpha-hydroxy acids and poly-hydroxy carboxylic acids, derivatives of retinoic acid, poly-hydroxy carboxylic acids, oxa acids, oxa diacids and mixtures thereof.

17. The method of claim 3, wherein said water-soluble organic acid is a salt of said organic acid, and wherein said salt is derived by neutralization with a base selected from the group consisting of triethanolamine arginine, lysine, potassium hydroxide, sodium hydroxide, lithium hydroxide and ammonium hydroxide.

18. A method for preparing a topical composition useful for delivering a water-soluble organic acid to the skin using an anhydrous vehicle, said method comprising:

encapsulating said water-soluble organic acid into one or more microsphere formed of a non-polar copolymer of a carbamate and an acrylate, and incorporating said one or more microspheres into an anhydrous vehicle to form an organic acid microsphere composition, and applying said organic acid microsphere composition to the skin;

wherein the presence of water activates said water-soluble organic acid microsphere composition causing said organic acid to elute from said one or more microspheres.

19. The method of claim 18, wherein said water-soluble organic acid is selected from the group consisting of alpha-hydroxy acids, beta-hydroxy acids, keto-acids, di-alpha-hydroxy acids and poly-hydroxy carboxylic acids, derivatives of retinoic acid, poly-hydroxy carboxylic acids, oxa acids, oxa diacids, and mixtures thereof.

20. The method of claim 18, wherein said water-soluble organic acid is a salt of said water-soluble organic acid, and wherein said salt is derived by neutralization with a base selected from the group consisting of triethanolamine arginine, lysine, potassium hydroxide, sodium hydroxide, lithium hydroxide and ammonium hydroxide.

* * * * *

UNITED STATES PATENT AND TRADEMARK OFFICE
CERTIFICATE OF CORRECTION

PATENT NO. : 5,962,018
DATED : October 5, 1999
INVENTOR(S) : Curtis et al.

It is certified that error appears in the above-identified patent and that said Letters Patent is hereby corrected as shown below:

Column 7,
Line 59, after "20" delete the "wt%.%" and insert therefor -- wt.% --.

Column 8,
Line 4, delete "oxa-diacids" and insert therefor -- oxa diacids, --.
Line 7, after "acid" delete ", said method";
Line 14, after "or after" insert -- , --; and
Line 16, after "palmar", delete "and" and insert therefor -- or --.
Line 32, delete "oxa di-acids" and insert therefor -- oxa diacids, --
Line 40, delete "microspheres are" and insert therefore -- microsphere is --; and
Line 41, before "non-polar" insert -- a --.
Line 58, delete "moisterizers" and insert therefor -- moisturizers --; and
Line 59, after "insect repellents" insert -- , --.

Column 9,
Line 1, delete "and poly-hydroxy carboxylic acids".
Line 5, delete "microsphere" and insert therefor -- microspheres --.
Line 7, delete "and poly-hydroxy carboxylic acids"; and
Line 9, after "oxa diacids" insert -- , --.
Line 18, delete ", said method";
Line 20, after "acrylate," delete "and";

Column 10,
Line 6, delete "water-soluble"; and
Line 7, after "said", insert -- water-soluble --.
Line 12, delete "and poly-hydroxy carboxylic acids".

Signed and Sealed this

Eighteenth Day of March, 2003

JAMES E. ROGAN
*Director of the United States Patent and Trademark Office*